United States Patent [19]

Rossmy

[11] 4,044,038

[45] Aug. 23, 1977

[54] PROCESS FOR THE MANUFACTURE OF AT LEAST SUBSTANTIALLY BALANCED ORGANOPOLYSILOXANE MIXTURES WITH SILYL HALIDE GROUPINGS

[75] Inventor: Gerd Rossmy, Essen-Werden, Germany

[73] Assignee: Th. Goldschmidt AG, Essen, Germany

[21] Appl. No.: 683,085

[22] Filed: May 4, 1976

Related U.S. Application Data

[63] Continuation of Ser. No. 517,319, Oct. 23, 1974, abandoned.

[30] Foreign Application Priority Data

Oct. 24, 1973 Germany .............................. 2353166

[51] Int. Cl.² ................................................ C07F 7/08

[52] U.S. Cl. ...................... 260/448.2 P; 260/448.2 E
[58] Field of Search ................... 260/448.2 E, 448.2 P

[56] References Cited

U.S. PATENT DOCUMENTS

| | | | |
|---|---|---|---|
| 2,421,653 | 6/1947 | Sauer | 260/448.2 P X |
| 3,661,962 | 5/1972 | Geipel | 260/448.2 E |

Primary Examiner—Paul F. Shaver
Attorney, Agent, or Firm—Toren, McGeady and Stanger

[57] ABSTRACT

The invention relates to a process for the preparation of at least substantially equilibrated organopolysiloxane mixtures with silyl halide groupings through redistribution of siloxane and silyl halide groupings in the process of equilibrating catalysts, if necessary at elevated temperatures.

13 Claims, No Drawings

PROCESS FOR THE MANUFACTURE OF AT LEAST SUBSTANTIALLY BALANCED ORGANOPOLYSILOXANE MIXTURES WITH SILYL HALIDE GROUPINGS

This is a continuation of application Ser. No. 517,319, filed Oct. 23, 1974, now abandoned.

Organopolysiloxanes with terminal silyl halide groups can be used as such, for instance for the impregnating of substrates, or can play an important part as intermediate products in industry. Preference is given to SiCl groups and compound mixtures which, with regard to their distribution of molecular weight as well as in the distribution of different siloxane structures within the molecule, can be manufactured in a reproducible manner. This objective is achieved, among other methods, through equilibrating reactions involving as catalysts for instance $HFeCl_4$, $SbCl_5$, $H_2SO_4$ as well as sulfonic acids and in which the sulfonic acids and $H_2SO_4$ are incorporated into the siloxane structure as reactive groups. Pertinent examples are described in the German Disclosures 2,059,546, 2,059,554, as well as in the German Application 1,174,509 laid open for public inspection and in the U.S. Pat. No. 3,115,512.

Organopolysiloxanes with reactive terminal groups can be used, among other applications, for the preparation of block copolymers in which the bonding is brought about via SiOc or SiC bonds, as well as for the preparation of organopolysiloxanes with terminal hydroxyl groups, acyloxy groups, or possibly substituted amino groups. This listing is however incomplete in view of the fact that the SiCl group is highly reactive and that, in lieu of the chlorine atom, there can be used many other partly per se reactive substituents. The catalysts contained in the siloxanes with reactive terminal groups according to the state of the art frequently result, during the abovementioned reactions, in secondary reactions that are sometimes put up with, that may however have a disturbing effect in certain reactions or applications methods. Damaging effects are generated in particular by the residues of catalytically active groups or compounds in those end products, which contain SiOC, SiOH, or SiN bonds, in view of the fact that the shelf life of the products is being limited as a result.

The object of the instant invention is to find a catalyst system generating the equilibrium, which is catalytically highly effective, can be readily separated out after equilibrium has been established, and that, as far as the secondary reactions are concerned, has no disturbing effect.

This object is achieved by the process in accordance with the invention in that mixtures of organohalogen silanes and organopolysiloxanes or mixtures of organopolysiloxanes with terminal silyl halide groups which, with regard to the distribution of their molecular weight and/or the distribution of the individual siloxane structures do not correspond to the statistical equilibrium, are being treated with mixed catalysts made of halogen hydracid and peralkylated acid amide in quantities of 0.002 to 0.2 mole/siloxane bond and that the catalyst system is subsequently removed by means of phase separation.

The advantageous properties of the organopolysiloxanes are frequently being obtained already at the moment when the equilibrating reaction has not yet ran its full course while the mixtures are however at least substantially in a state of equilibrium.

In that process one uses preferably a mixed catalyst composed of HCl and dimethyl formamide. As to the halogen atom, the halogen hydracid corresponds preferably to the silyl halogen groups.

The mixed catalysts of the peralkylated acid amide with the halogen hydracids are present in the form of liquid mixtures or complexes with the ratio of peralkylated acid amide to halogen hydracid being able to vary within wide limits. As stated already, dimethyl formamide is the peralkylated acid amide that is to be used preferably. In that case it is particularly advantageous to use solutions, saturated at room temperature, of halogen hydracid and dimethyl formamide, which corresponds substantially to the dimethyl formamide · 2 halogen hydracid complex. It is however likewise possible to use complex compounds containing excess as well as inadequate amounts of dimethyl formamide. One uses preferably molar ratios of halogen hydracid to dimethyl formamide > 1, in particular if one operates at elevated pressure.

The process in accordance with the invention is preferably performed at elevated temperatures, in particular temperatures > 50° to 110° C. Particularly preferred are temperatures above 70° C. The upper limit of the equilibrating temperature is set by the heat of decomposition of the complex mixed catalysts. In that process, the particularly preferred reaction temperature is at about 100° C.

The achieving of the equilibrium is promoted and brought about particularly rapidly if the process is performed at elevated pressure. In that case, it is sufficient to operate in closed off reaction vessels and under the intrinsic pressure of the solutions of halogen hydracid in peralkylated acid amide that occurs at the respective process temperature. One thereby prevents that quantities of halogen hydracid that are important for the catalytic effect escape from the reaction mixture at elevated temperature.

Although we referred above consistently to dimethyl formamide as the peralkylated acid amide, this is not the only suitable peralkylated acid amide. Likewise suitable are peralkylated amides whose alkyl groups have preferably not more than 4 carbon atoms. Particularly suitable proved to be in that connection dimethyl acetamide and hexamethyl phosphoric acid triamide. Other products, such as N-N'-tetramethyl urea, diethyl formamide, N-dimethylethyl phosphonic acide amide, N-N'-tetraethyl urea, diethyl acetamide can likewise be used. On account of the solubility relations, such compounds can also be used mixed with dimethyl formamide. (Solid catalysts require extended reaction times.)

In a further development of the process in accordance with the invention, the equilibrating is achieved not only by the complexes described thus far, but one uses additionally in per se known manner iron halide catalysts or their complex compounds with halogen hydracid. Compounds of this type are, respectively, $FeX_3$ and $HFeX_4$ where X is preferably Cl. One can use also other iron compounds capable of converting in the reaction mixture into $HFeX_4$ such as for instance ferric oxide and corresponding oxide hydrates.

The equilibrating process can be performed in several stages. In that case, the equilibrating with the complex iron compounds is preferably performed in the initial stage.

The quantity of the mixed catalysts to be used is generally in the range of 0.002 to 0.2 mole/siloxane bond in the mixture. A particularly preferred quantity is 0.01 to 0.1 mole/siloxane bond in the mixture. If one uses in addition FeCl₃ that, as stated above, acts also in this case presumably in the form of the complex acid HFeCl₄ there suffice quantities of 1 ppm. to 1 weight percent, preferably 0.001 to 0.1 weight percent, of this iron compound in combination with the abovementioned quantities of the mixed catalysts in accordance with the invention.

Inert solvents can be included in the equilibrating reaction in accordance with the invention. In view of the fact that the reaction mixture is heterogenous, one is successful with a simple separation of the mixed catalysts and the dimethyl formamide, possibly present in excess, by ordinary phase separation.

From the German Patent 1,285,471 it is known to manufacture organopolysiloxanes with terminal silyl halide groups, among others, in the presence of a dimethyl formamide. In that case, however, the dimethyl formamide serves as a reaction medium for the hydrolysis of the chlorosilanes. An equilibrium is not achieved.

The British Patent 1,040,147 does not likewise describe the preparation of organopolysiloxanes with terminal silyl halide groups in the presence of dimethyl formamide, however not in the complex form of the mixed catalyst used in accordance with the invention. The British Patent deals rather with the telomerization reaction. The objective to be achieved in that reaction are molecularly uniform halogen siloxanes, however not mixtures in equilibrium.

The organopolysiloxane mixtures, obtained in the process in accordance with the invention, having terminal silyl halide groups whose molecular and structural distribution corresponds at least substantially to the statistic equilibrium, can be illustrated for instance by the following formula I:

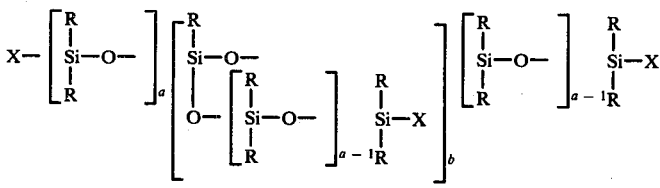

In this formula, R is preferably the methyl radical. However, R can partly denote also another radical that is inert to acid, possibly a substituted alkyl or aryl radical, such as:

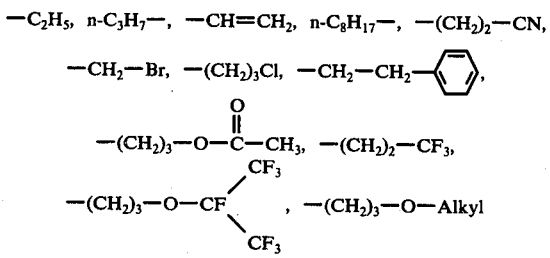

Additional data on substituents inert to acid in organopolysiloxanes and which can be brought into a state of equilibrium by means of acid catalysts can be found in the work by W. Noll "Chemie und Technologie der Silicone" publisher, "Verlag Chemie GmbH", 1968, as well as in the U.S. Pat. No. 3,115,512.

In the case of aryl radicals situated on the silicon atom one must reckon in the course of the equilibrating reaction to a certain extent with the separation of these radicals. $a$ was selected in such a way that, in the average molecule, there are 2 to 100, preferably 4 to 50 Si atoms and that the relationship of the R radicals in nontrifunctional Si atoms bonded to such radicals which are bonded to trifunctional Si atoms amounts preferably to at least 4. In that case, $b$ is 0 to 50, preferably 0 to 10. The R radical situated on the formally trifunctional Si atom may denote in whole or in part the radical —O₀.₅— having an intermolecular or an intramolecular connecting effect. In this case, the molecule contains therefore also tetrafunctional Si atoms. X is a halogen, preferably the chlorine or possibly the bromine radical. A portion of the radicals X can also be a triorganosiloxy radical, in particular the trimethyl siloxy radical.

As will be illustrated in the examples, one can prepare also halogen siloxanes consisting only of trifunctional Si atoms.

The following can be used as base substances to carry the process in accordance with the invention into effect:

a. Molecularly uniform organopolysiloxanes with silyl halide groups. It is however hardly likely that these products will be industrially used as basic ingredients in view of the fact that their preparation is too costly.

b. Mixtures of organohalogensilanes and organopolysiloxanes, in particular cyclic organopolysiloxanes. It may be assumed that the primary step consists in that case in a cleavage of the cyclosiloxane by the halogen hydracid, e.g.

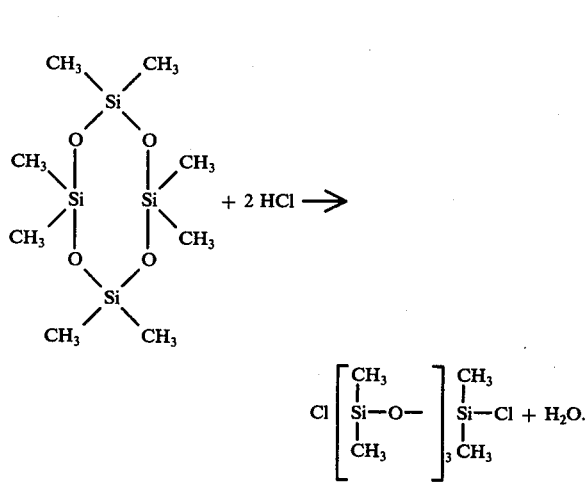

The water is being consumed initially preferably for the hydrolysis of the organohalogensilane. In the course of the equilibrating process in accordance with the invention, there is then achieved a redistribution of all Si—O—Si and Si—X bonds corresponding to the equilibrium.

c. Mixtures of organopolysiloxanes with or without silyl halide groups as can be obtained for instance through partial hydrolysis of organohalogen silanes. The overall composition of this mixture corresponds also in this case, as in the case of (a) and (b), to the average formula already discussed. The equilibrating modifies the distribution of the molecular weight as well as the distribution of individual siloxane building blocks in the molecules, however not the average composition.

The halogen siloxanes, prepared in equilibrated form as process products, can be used in accordance with the state of the art as described for instance in German Patents 1,495,961, 1,495,926, and 1,300,697. They are suitable for further conversion for the preparation of derivatives according to per se known processes, for instance with SiOC, SiOH, $$\text{SiOCR},\overset{\overset{\displaystyle O}{\|}}{}$$

and SiN groups. Their advantage in that case is the increased precision in reproducibility in that case and their improved shelf life.

The mixtures of substances prepared by the process in accordance with the invention are however not only intermediate products but can also be used directly, among other applications, for the hydrophobing of for instance pyrogenically obtained silicic acid, which can be used as a filler material. A silicic acid that has been pyrogenically produced and that is prepared with these compounds is particularly well suitable for producing silicone base skimmer emulsions that are still highly effective even in an alkaline medium.

The process in accordance with the invention is to be explained in greater detail by the following examples:

EXAMPLE 1

A siloxane mixture of the general formula

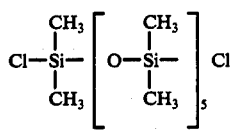

is being prepared by partial hydrolysis of dimethyl dichlorosilane. In the gas-chromatographic analysis, the peak of the octamethylcyclotetrasiloxane takes up approximately 35% of the overall area. This mixture is treated with a catalyst consisting of dimethyl formamide · 2 HCL in amounts of 0.02 mole/Si and heated, accompanied by stiring, to 100° C for six hours. The mixture is then allowed to dry and the catalyst phase is removed. The gas chromatogram shows a distribution of linear $\alpha\omega$dichloro polydimethyl siloxanes with a maximum area in the case of tetrasiloxane. Only 5.8% of the peak areas are still to be attributed to the cyclotetrasiloxane. The test is being repeated, the variant being that the reaction occurred in a closed ampulla accompanied by intense agitation. The share of octamethylcyclotetrasiloxane drops to 2.1% of the overall area. The area distribution expressed in percentages is illustrated in Table 1.

| Number of Si atoms in molecule | In chain form ($\alpha\omega$ dichloropoly siloxanes) | Cyclosiloxanes |
| --- | --- | --- |
| 1 | 0.9 | — |
| 2 | 5.9 | — |
| 3 | 12.1 | — |
| 4 | 13.5 | 2.1 |
| 5 | 12.3 | 1.0 |
| 6 | 10.5 | 0.2 |
| 7 | 8.8 | — |
| 8 | 7.1 | — |
| 9 | 5.8 | — |
| 10 | 4.7 | — |
| 11 | 3.9 | — |
| 12 | 2.8 | — |
| 13 | 2.1 | — |
| 14 | 1.5 | — |
| >14 | 4.8 | — |

A practically identical distribution was obtained by equilibrating the initial mixture with 0.01 weight-percent of FeCl₃ (+HCl)as well as by pressure-equilibration using the catalyst dimethyl formamide . 2 HCl under similar conditions, if one uses in lieu of the siloxane mixture of this example molecularly uniform $\alpha\omega$-dichlorododecamethyl hexasiloxane, or a mixture of 1 mole dimethyl dichlorosilane and 1.25 mole octamethylcyclotetrasiloxane. This proves the presence of a genuine equilibrium state with partidipation of the Si—O—Si and the Si—Cl bonds.

EXAMPLE 2

In the case of halogen siloxanes having a higher molecular weight, it is not possible to provide scientifically precise proof for the achieving of the equilibrium state. This holds true in particular also in those cases in which the organopolysiloxane contains trifunctional or tetrafunctional Si atoms. In this case, the conversion of the halogen siloxanes into siloxane polyether block polymers (which can be used as foam stabilizers to arrest the foaming of polyurethane) provides a sensitive indicator for the progress of the rearrangement reactions leading to a rapprochement to the equilibrium of the molecular weight distribution.

For the tests of this example, there was partially hydrolized in each case a mixture of 299 g methyltrichlorosilane and 3,302 g dimethydichlorosilane by instilling of a such a quantity of H₂O that, following heating at 100° C, one obtains a chloropolymethylene siloxane having 1.86 . 10⁻³ g-atoms of Cl/g. This product corresponds to a siloxane mixture of the formula I, in which R = Ch₃, a = 5.4, and b = 2.

In one instance, the hydrolysis is performed with a silane mixture containing respectively 0.01 and 0.0001 weight-percent of FeCl₃, with respect to the product of the hydrolysis. In other cases silanes purified by distillation were used. The equilibrating by using as catalyst dimethyl formamide . 2 HCl occurs at 100° C during a period of six hours and at a catalyst concentration of 0.02 mole dimethyl formamide/Si. A repetition of this test using 0.2 mole dimethyl formamide/Si produces a chlorosiloxane having practically identical properties.

The following table shows the products obtained under different conditions:

| Addition of FeCl₃ at the hydrolysis | Equilibration using DMF . 2 HCl in an open vessel | Equilibration using DMF . 2 HCl in a closed vessel |
| --- | --- | --- |
| A — | — | — (Control test) |
| B — | + | — |
| C — | — | + |

| Addition of FeCl₃ at the hydrolysis | Equilibration using DMF . 2 HCl in an open vessel | Equilibration using DMF . 2 HCl in a closed vessel |
| --- | --- | --- |
| D + (0.01 weight-%) | − | + |
| E + (0.001 weight-%) | − | + |

The chlorosiloxanes A to D are caused to react with a polyether mixture obtained by addition of propylene and ethylene oxide in statistic sequence to n-butanol, the addition terminating by adding 2 mole propylene oxide. The molecular weight of the polyoxyalkylene block was 1,980, the equilibrium ratio of propylene oxide: ethylene oxide was 51:59. For the purpose of the reaction, 50 g of the siloxane were blended with the azeotropically dried polyether dissolved in 770 ml toluene. To each SiCl group there correspond 0.95 mole polyether monool. In addition, the solution contains also 0.17 mole of isopropanol. The reaction temperature is 50° C. After 30 minutes, NH₃ is introduced into the solution until alkaline reaction, the solution is filtered and the block polymers are isolated by evaporation. For the purpose of stabilization, 0.4 weight-percent of butyl ethanol amine are added to the product. As a measure for the approaching of the equilibrium, one can use the viscosity of the block polymer as well as the density of a polyurethane foam prepared in accordance with the following recipe by using the block polymer. The following foam recipe was used:

100.00 parts by weight of polyol having an OH number of 47.5 and an ethylene oxide to propylene oxide ratio of 5:95, prepared by the addition alkylene oxide to glycerin
4.05 parts by weight of H₂O
3.00 parts by weight of trichlorofluoromethane
0.80 parts by weight of siloxane polyether block polymer
0.27 parts by weight of tin octoate
0.15 parts by weight of dimethyl ethanol amine
0.05 parts by weight of N-ethyl morpholine
52.50 parts by weight of toluylene diisocyanate T 80

| Cl siloxane used | Viscosity of the block polymer at 20° C (cP) | Density of the foam (prepared at a pressure of 760 mm) (kg/m³) |
| --- | --- | --- |
| A | 536 | Foam unusable due to collapse |
| B | 850 | 24.5 |
| C | 960 | 22.9 |
| D | 1,374 | 22.0 |
| E | 1,170 | 22.2 |

The foam stabilizers prepared from B to E were stored at 80° C for four weeks. Subsequently, their properties in the manufacture of foams proved to be completely unchanged, that is to say, densities were achieved that were identical to those that had been achieved initially.

Foam stabilizers containing identical overall compositions and that had veen prepared by using 1.6 g sulfuric acid/Si atom or with 0.01 weight-percent of iron chloride/equilibrated chlorosiloxane show, following storage, a rise of respectively 0.6 and 4.2 kg/m³.

EXAMPLE 3

The silane

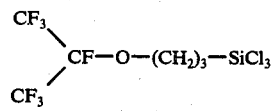

is converted by partial hydrolysis into a chlorosiloxane mixture corresponding to the general formula $C_3F_7$—O—$(CH_2)_3Si$—(Cl)—O In a distillation performed at a pressure of 14 Torr and a temperature of the bath of 100° C, 40 percent-by-weight of monomer silane can be volatilized from this mixture. If the identical mixture is treated with a 45 percent solution of HCl in dimethylformamide (0.03 mole dimethylformamide/Si) at 100° C for 10 hours, one can volatilize by distillation only 7 percent-by-weight of monomer silane. This evidences the completed incorporation of the silane in the chlorosiloxane through redistribution.

EXAMPLE 4

One heats in ampoules equimolar mixtures of hexamethylcyclotrisiloxane and silanes or chlorosiloxanes at 95° C for 5 hours accompanied by the addition of 0.015 mole of the catalyst dimethylformamide . 2 HCl. One uses the following as silanes and chlorosiloxanes, respectively:

a. Methyl vinyl dichlorosilane
b. α, ω-dichlorohexamethyl trisiloxane
c. Bromomethyl methyldichlorosilane
d. Phenyl methyl dichlorosilane
e. Cyancethylmethyl dichlorosilane
f. γ-acyoxypropyl methyldichlorosilane
g. Octadecyltrichlorosilane Following cooling of the ampoules they were opened and the catalyst phase separated. The siloxane mixture is examined by gas chromatography. In these ampoules there occurred a complete reaction of the charged cyclotrisiloxane. There remain only traces of the initial silanes. The gas chromatogram indicates a distribution of siloxanes with terminal chlorine groups as can be expected in the case of a statistic equidistribution.

What is claimed is:

1. In a process of preparing at least approximately equilibrated organopolysiloxane mixtures having silylhalide groups, by redistribution of siloxane and silylhalide groups, wherein mixtures of organohalogensilanes and organopolysiloxanes or mixtures of organopolysiloxanes with terminal silylhalide groups are equilibrated in the presence of an equilibration catalyst, the molecular weight distribution or the distribution of the individual siloxane structures of the mixtures to be treated deviating from the statistical equilibrium, the improvement which comprises that the equilibration treatment is performed in the presence of an equilibration catalyst which is a mixed catalyst comprising
a. hydrogen halide acid and
b. peralkylated acid amide,
the amount of said mixed catalyst being in the range of 0.002 to 0.2 mole per siloxane bond, said mixed catalyst being removed from the system after the equilibration treatment by phase separation.

2. The improvement of claim 1, wherein said acid of a. is HCl, while said amide of
b. is dimethylformamide.

3. The improvement of claim 1, wherein the equilibration treatment is carried out at a temperature of > 50° to 110° C.

4. The improvement of claim 1, wherein the equilibration treatment is carried out under a pressure which is above atmospheric pressure.

5. The improvement of claim 1, wherein the equilibration treatment is carried out in a closed reaction vessel at that pressure which is the corollary of the temperature of the reaction mixture.

6. The improvement of claim 1, wherein said mixed catalyst essentially consists of dimethylformamide . 2 HCl and said equilibration treatment is performed at about 100° C.

7. The improvement of claim 1, wherein said silylhalide groups are SiCl groups.

8. The improvement of claim 1, wherein said catalyst additionally contains $HFeCl_4$ in amounts of 1 ppm to 1 percent by weight, calculated on each siloxane bond in the mixture to be equilibrated.

9. The improvement of claim 8, wherein 0.001 to 0.1 percent by weight of $HFeCl_4$ is used.

10. The improvement of claim 1, wherein the equilibration treatment is performed in stage wise manner.

11. The improvement of claim 10, wherein the equilibration treatment is initiated with said $HFeCl_4$ whereafter the equilibration treatment is continued and terminated with said mixed catalyst of (a) and (b) in one or several stages.

12. The improvement of claim 1, wherein said mixed catalyst of (a) and (b) is in the form of liquid mixtures or complexes.

13. The improvement of claim 1, wherein said mixed catalyst is a room-temperature saturated solution of hydrogen halide acid in dimethylformamide.

* * * * *